(12) United States Patent
Burkett

(10) Patent No.: US 7,736,625 B2
(45) Date of Patent: Jun. 15, 2010

(54) LIGHT STABILIZED IN VIVO STAIN COMPOSITION AND METHOD OF MANUFACTURE

(75) Inventor: Douglas D. Burkett, Gilbert, AZ (US)

(73) Assignee: Zila, Inc., Fort Collins, CO (US)

( * ) Notice: Subject to any disclaimer, the term of this patent is extended or adjusted under 35 U.S.C. 154(b) by 0 days.

(21) Appl. No.: 12/330,345

(22) Filed: Dec. 8, 2008

(65) Prior Publication Data

US 2009/0092552 A1  Apr. 9, 2009

Related U.S. Application Data

(63) Continuation of application No. 10/487,329, filed as application No. PCT/US01/26805 on Aug. 28, 2001, now Pat. No. 7,462,346.

(51) Int. Cl.
*A61B 10/00* (2006.01)
*A61B 5/00* (2006.01)
*A61B 8/00* (2006.01)

(52) U.S. Cl. .................. 424/9.6; 424/1.11; 424/1.65; 424/9.1; 424/1.81; 549/1; 549/31; 549/14

(58) Field of Classification Search ................ 424/1.11, 424/1.65, 1.81, 9.1, 9.3, 9.4, 9.5, 9.6, 9.7, 424/9.8; 549/1, 2, 3, 14, 31, 34, 37
See application file for complete search history.

(56) References Cited

U.S. PATENT DOCUMENTS

| 4,321,251 | A | 3/1982 | Mashberg |
| 6,086,852 | A | 7/2000 | Burkett |
| 6,194,573 | B1 | 2/2001 | Burkett |
| 6,372,904 | B2 | 4/2002 | Burkett |
| 6,830,743 | B1 | 12/2004 | Burkett |
| 7,462,346 | B2 * | 12/2008 | Burkett ...................... 424/9.6 |
| 2004/0247695 | A1 | 12/2004 | Burkett |

FOREIGN PATENT DOCUMENTS

WO   WO 99/25388   5/1999

OTHER PUBLICATIONS

Havelcova et al, Photophysical properties of thiazine dyes in aqueous solution and in micelles, Dyes and Pigments, 2000, vol. 44, pp. 49-54.

* cited by examiner

*Primary Examiner*—D L Jones
(74) *Attorney, Agent, or Firm*—Jeffer Mangels Butler & Marmaro LLP

(57) ABSTRACT

Photochemical demethylation reactions in solutions of thiazine dyes, in which the dye molecules act as both sensitizer and substrate, are reduced by quenching triple-state dye molecules, returning them to the unreactive ground state.

19 Claims, No Drawings

LIGHT STABILIZED IN VIVO STAIN COMPOSITION AND METHOD OF MANUFACTURE

CROSS-REFERENCE TO RELATED APPLICATIONS

This application is a continuation of U.S. patent application Ser. No. 10/487,329, filed Feb. 17, 2004, which is a U.S. national phase entry application of PCT/US01/26805, filed Aug. 28, 2001, all of which are incorporated herein in their entireties by this reference.

This invention relates to light-stabilized thiazine dye biological stain compositions, illustratively, the tolonium chloride ("TC") dye compositions disclosed in my U.S. Pat. No. 6,086,852.

In another respect the invention concerns methods of manufacturing such compositions.

In particular the invention contemplates light-stabilized tolonium chloride ("TC") dye compositions and their manufacture.

BACKGROUND OF THE INVENTION

As far as known, prior workers, such as Mashberg (U.S. Pat. No. 4,321,251), who instigated the use of TC for in vivo identification of dysplasia, used prior art dye products in which the conformational isomers of TC plus the N-demethylation and N,N-demethylation derivatives of the conformational isomers were less than 80% of the dye composition and in which the two N-demethylation derivatives of the conformational isomers, formed greater than about 20% % of the dye composition. According to my information, prior workers were unaware of the exact composition of their "TC" products and manufacturers of prior art TC products were unable to reproducibly prepare them. In fact, the prevalent literature description of the quality of TC was simply that it have "good color value". The Biological Stain Commission specifies an analytical titration procedure for determining only the "organic dye content" of the TC material. The prior art use of such loosely defined "TC" resulted in anomalous clinical observations and serious problems in obtaining necessary regulatory clearances to manufacture and market such products for use in human diagnostic procedures.

In addition to the problem of variable initial composition, prior art TC and other thiazine biological stains were subject to time-related variations in composition. For example, Dean et al. in "Stains Technology", Vol. 32, No. 1, pp. 35 et seq. (1977) recommended that thiazine dyes in methanolic solutions should be refrigerated to prevent further oxidative N-demethylation. Liao, et al. reported in "Stains Technology", Vol. 57, No. 1, pp. 23 et seq. (1982) that reduction in methylene blue content by precipitation from methanolic Wright's stain solution could be markedly decreased by simultaneous addition of diethylamine hydrochloride and dimethylamine hydrochloride.

In my U.S. Pat. No. 6,086,852, I describe a process for reproducibly manufacturing high-quality TC products initially having a high proportion of the conformational isomers with respect to the N-demethylation products of such isomers. While exclusion of contact with air and avoidance of high temperatures retard oxidative N-demethylation of the conformational isomers, it is observed that, in the absence of free radical scavengers, such as metal ions, alcoholic solutions of this TC product undergo light-induced or photochemical N-demethylation. Illustrative TC dyes, incorporated by reference from U.S. Pat. No. 6,086,852 are

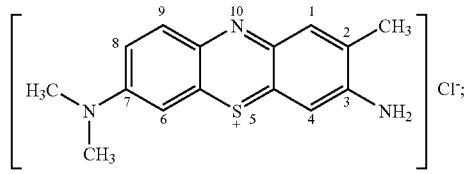
(I) Peak 8

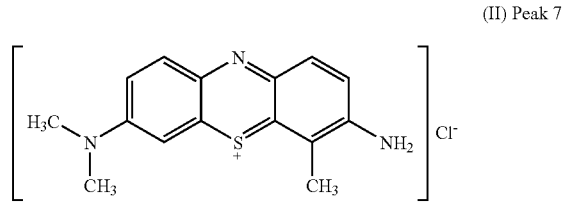
(II) Peak 7

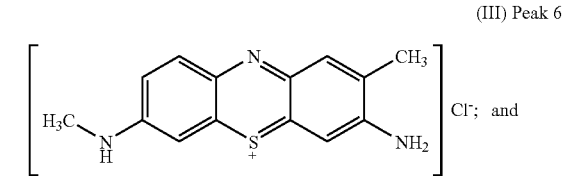
(III) Peak 6

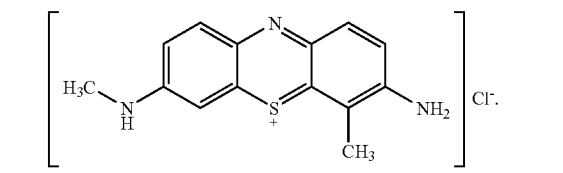
(IV) Peak 5

BRIEF DESCRIPTION OF THE INVENTION

I have now discovered improvements in solutions of thiazine dyes, wherein molecules of the dye act as both the sensitizers and substrates in photochemical oxidative N-demethylation reactions, in which reactions some of said dye molecules absorb light and are converted to the singlet state, some of said singlet-state dye molecules react with unactivated substrate dye molecules to form triplet state molecules by intersystem crossing, some of said triplet-state molecules react with ambient ground-state oxygen to produce singlet-state oxygen molecules, and some of said singlet-state oxygen molecules demethylate ground-state dye molecules. My improvements, which substantially reduce said demethylation comprises quenching at least some of the triplet-state dye, preferably by incorporating into said solution a free radical scavenger, e.g., a metal ion, thus returning the triplet-state dye molecules to the unreactive ground-state.

DETAILED DESCRIPTION OF THE INVENTION

Oxidative N-demethylation of a thiazine dye is envisioned to occur as illustrated below for the demethylation of TC:

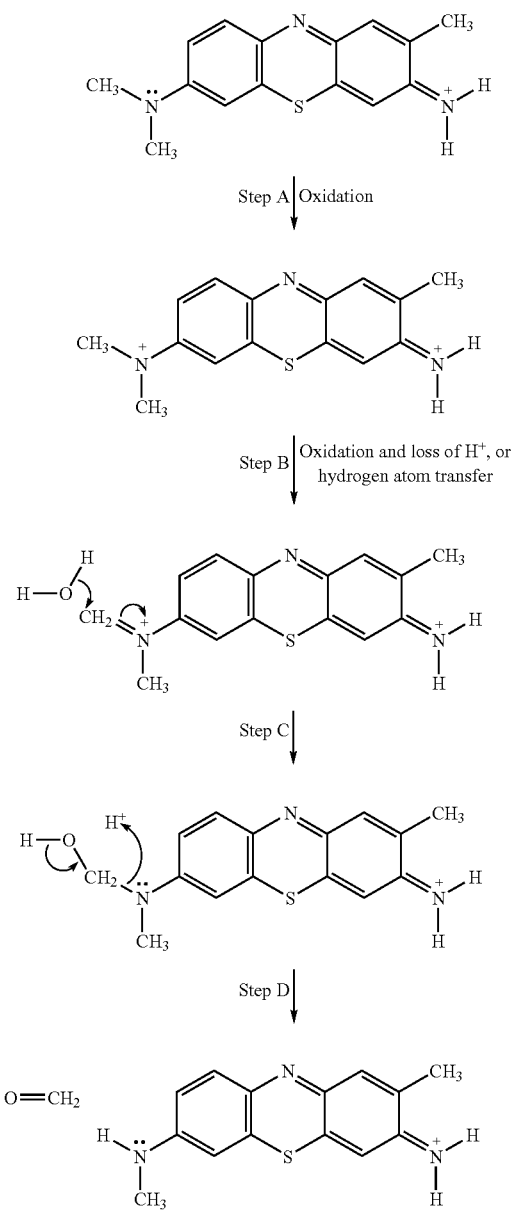

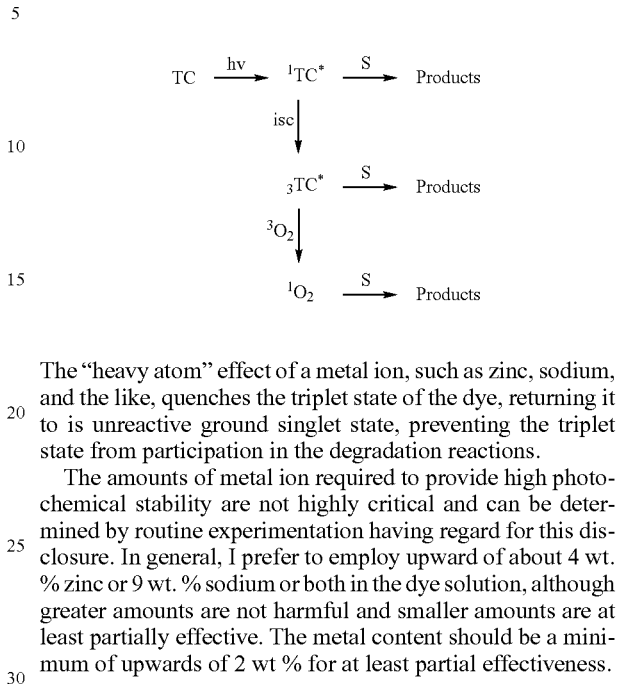

In Steps A and B, an electron is removed from the TC to produce a radical cation, which is then oxidized again and loses a proton to form an iminium ion. Subsequently, the iminium ion undergoes nucleophilic attack by water (Step C) to produce the carbinolamine intermediate, in which there is a hydroxyl group and an amino group attached to the same carbon atom. The carbinolamine is unstable, and loss of the amine (Step D) liberates formaldehyde and monodemethylated TC. In the case of demethylation of methylene blue, this would correspond to the formation of Azure C from Azure A.

In photochemical demethylation reactions, TC apparently acts both as the sensitizer and the substrate in photochemical reactions, i.e., in the absence of free-radical scavengers, it brings about its own photodecomposition. Thus, TC absorbs light and becomes a "photosensitizer" and brings about a direct reaction of the TC in its singlet excited state with another TC molecule "substrate." The substrate molecule reacts with the triplet state of the dye, formed by intersystem crossing (isc). Singlet oxygen is formed by reaction of ground state oxygen with the triplet state of the dye, followed by reaction of singlet oxygen with the substrate.

The "heavy atom" effect of a metal ion, such as zinc, sodium, and the like, quenches the triplet state of the dye, returning it to is unreactive ground singlet state, preventing the triplet state from participation in the degradation reactions.

The amounts of metal ion required to provide high photochemical stability are not highly critical and can be determined by routine experimentation having regard for this disclosure. In general, I prefer to employ upward of about 4 wt. % zinc or 9 wt. % sodium or both in the dye solution, although greater amounts are not harmful and smaller amounts are at least partially effective. The metal content should be a minimum of upwards of 2 wt % for at least partial effectiveness.

EXAMPLES

The following examples illustrates the practice of the preferred embodiments of the invention and are not intended to serve as limitations on the scope thereof, which is defined only in the appended claims.

Example 1

This example illustrates the light-instability of a TC product with negligible content of metal ions.

A sample of the TC product is prepared in accordance with Example 1 of my U.S. Pat. No. 6,086,852, incorporated herein by reference, and further purified by preparative high performance liquid chromatography. The total metal content of this sample is less than 0.2 wt. %.

An aliquot of this purified TC product sample is deep-blue in color. After standing overnight in the laboratory, exposed to ambient incandescent light, the solution becomes colorless.

Example 2

The sample of Example 1 except containing about 4 wt % Zn (as zinc chloride) and 9% Na (as sodium chloride) in the solution is essentially completely stable in the presence of incandescent light.

Example 3

The procedures of Examples 1 and 2 are repeated using methylene blue, Azure A and Azure C instead of TC. Similar results are obtained.

Example 4

The procedures of Example 1-3 are repeated except using only zinc chloride in solution and only sodium chloride in solution. Equivalent results are obtained.

Example 5

The procedures of Example 14 are repeated except that soluble salts of magnesium, chromium and silicon are used instead of zinc and sodium salts. Similar results are obtained.

Having described my invention in such terms as to enable one skilled in the art to understand and practice it and, having identified the presently preferred embodiments thereof, I claim:

1. A method for reducing N-demethylation reactions in a thiazine dye solution, wherein the thiazine dye comprises:

(1) the compounds having the structures:

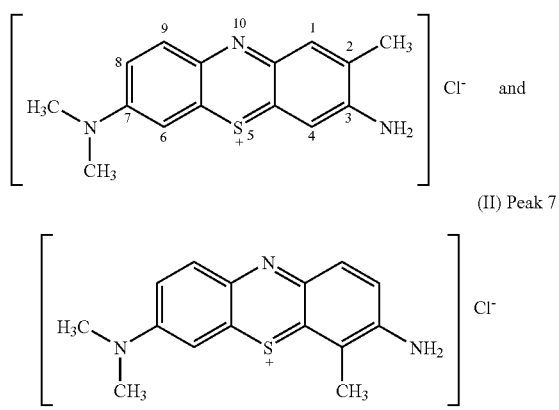

(2) the compounds having the structures:

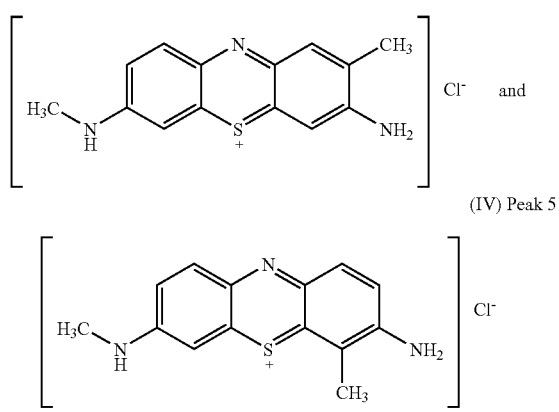

the ratio of the combined areas of the 254 nm HPLC peaks representing the compounds in (1) to the combined areas of the peaks representing the N-demethylation derivatives in (2) being at least 6:1;
wherein molecules of the dye act as both the sensitizers and substrates in photochemical oxidative N-demethylation reactions in a thiazine dye solution, in which reactions at least a portion of the dye molecules absorb light and are converted to the singlet state,
    at least a portion of the singlet-state dye molecules form triplet state molecules by intersystem crossing,
        at least a portion of the triplet-state molecules react with ambient ground-state oxygen to produce singlet-state oxygen molecules, and
        at least a portion of the singlet-state oxygen molecules N-methylate ground-state dye molecules,
the method comprising adding, after the thiazine dye solution is formed, a metal ion to the solution, wherein the metal ion quenches some of the triplet state dye molecules and returns them to the unreactive ground state.

2. The method of claim 1 wherein the metal ion is a heavy atom.

3. The method of claim 1, wherein said metal ion is a zinc ion.

4. The method of claim 1, wherein said metal ion is a sodium ion.

5. The method of claim 1, wherein the metal ions are both zinc and sodium ions.

6. A method for at least partially reducing the oxidative demethylation of a thiazine dye, the method comprising the steps of:
providing a thiazine dye in solution; and
adding, after the thiazine dye solution is formed, a metal ion to the thiazine dye solution;
wherein the thiazine dye comprises:

(1) the compounds having the structures:

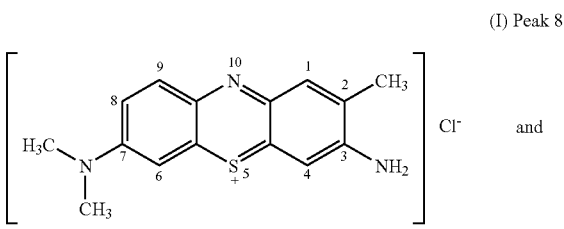

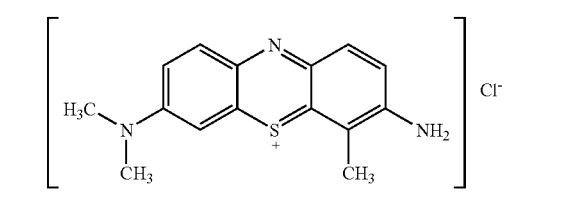

(2) the compounds having the structures:

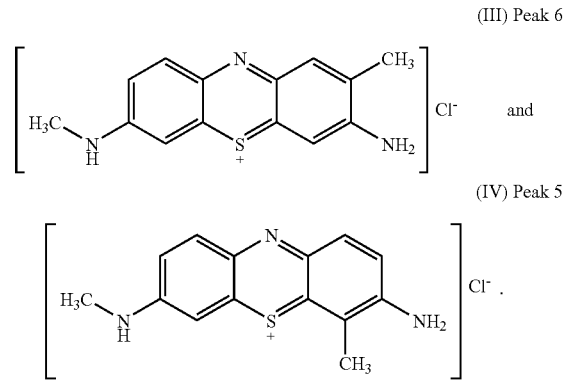

the ratio of the combined areas of the 254 nm HPLC peaks representing the compounds in (1) to the combined areas of the peaks representing the compounds in (2) being at least 6:1;

and wherein the metal ion quenches the thiazine dye to at least partially reduce the oxidative demethylation of the thiazine dye.

7. The method of claim 6, wherein the metal ion is a heavy atom.

8. The method of claim 6, wherein the total metal content of the thiazine dye solution is less than 0.2% by weight.

9. The method of claim 6, wherein the step of adding the metal ion to the thiazine dye solution produces a thiazine dye solution comprising about 2% by weight or more of the metal ion.

10. The method of claim 6, wherein the metal ion is any one or a combination of the compounds selected from the group consisting zinc, sodium, magnesium, chromium and silicon.

11. The method of claim 10, wherein the metal ion is selected as a combination of zinc and sodium.

12. The method of claim 6, wherein the metal ion is provided as a salt.

13. The method of claim 10, wherein the thiazine dye solution comprises about 4% by weight zinc chloride and 9% by weight sodium chloride.

14. A method for reducing N-demethylation reactions in a thiazine dye solution, wherein the thiazine dye comprises: the compounds having the structures

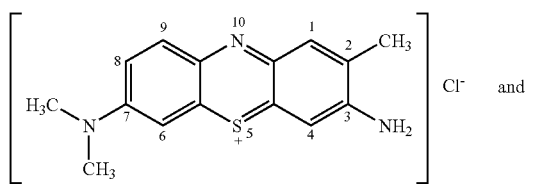

(I) Peak 8

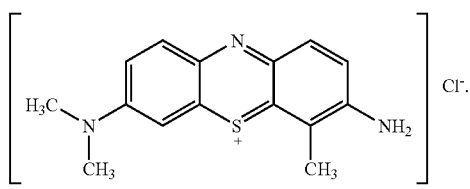

(II) Peak 7 in which (a) comprises at least 58% of the total organic dye content of the composition;

wherein molecules of the dye act as both the sensitizers and substrates in photochemical oxidative N-demethylation reactions, in which reactions at least a portion of the dye molecules absorb light and are converted to the singlet state, at least a portion of the singlet-state dye molecules form triplet state molecules by intersystem crossing, at least a portion of the triplet-state molecules react with ambient ground-state oxygen to produce singlet-state oxygen molecules, and at least a portion of the singlet-state oxygen molecules N-methylate ground-state dye molecules, the method comprising adding, after the thiazine dye solution is formed, a metal ion to the solution, wherein the metal ion quenches some of the triplet state dye molecules and returns them to the unreactive ground state.

15. The method of claim 14 wherein the metal ion is a heavy atom.

16. The method of claim 14, wherein the metal ion is a zinc ion.

17. The method of claim 14, wherein the metal ion is a sodium ion.

18. The method of claim 14, wherein the metal ions are both zinc and sodium ions.

19. A method for at least partially reducing the oxidative demethylation of a thiazine dye, the method comprising the steps of:

providing a thiazine dye in solution; and adding, after the thiazine dye solution is formed, a metal ion to the thiazine dye solution;

wherein the thiazine dye comprises:
the compounds having the structures

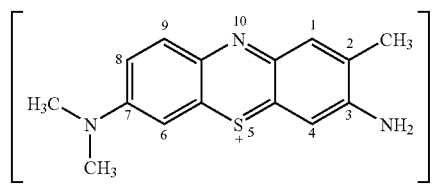

(I) Peak 8

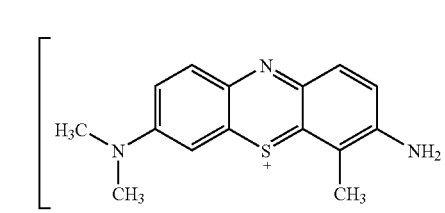

(II) Peak 7 in which (a) comprises at least 58% of the total organic dye content of the composition;

wherein the metal ion quenches the thiazine dye to at least partially reduce the oxidative demethylation of the thiazine dye.

* * * * *